United States Patent
Hopkins

(10) Patent No.: US 10,849,690 B2
(45) Date of Patent: Dec. 1, 2020

(54) TOOL FOR FIXED CUSTOMISED RELATIVE ALIGNMENT OF ADJUSTABLE ORTHOPEDIC DEVICES

(71) Applicant: Zimmer, Inc., Warsaw, IN (US)

(72) Inventor: Andrew Rolfe Hopkins, Winterthur (CH)

(73) Assignee: Zimmer, Inc., Warsaw, IN (US)

( * ) Notice: Subject to any disclaimer, the term of this patent is extended or adjusted under 35 U.S.C. 154(b) by 31 days.

(21) Appl. No.: 15/956,502

(22) Filed: Apr. 18, 2018

(65) Prior Publication Data

US 2018/0303551 A1    Oct. 25, 2018

Related U.S. Application Data

(60) Provisional application No. 62/488,499, filed on Apr. 21, 2017.

(51) Int. Cl.

| | | |
|---|---|---|
| *A61B 17/17* | (2006.01) | |
| *A61B 34/10* | (2016.01) | |
| *A61B 17/56* | (2006.01) | |
| *A61F 2/46* | (2006.01) | |
| *A61F 2/30* | (2006.01) | |
| *A61F 2/40* | (2006.01) | |

(52) U.S. Cl.
CPC .......... *A61B 34/10* (2016.02); *A61B 17/1778* (2016.11); *A61B 17/56* (2013.01);
(Continued)

(58) Field of Classification Search
CPC . A61B 17/17; A61B 17/1778; A61B 17/1746; A61B 34/10; A61B 17/56; A61B 17/1742; A61F 2002/4668; A61F 2002/4677; A61F 2002/4687; A61F 2/4684
(Continued)

(56) References Cited

U.S. PATENT DOCUMENTS

| 6,045,581 A | 4/2000 | Burkinshaw |
|---|---|---|
| 6,398,815 B1 | 6/2002 | Pope |
| (Continued) | | |

FOREIGN PATENT DOCUMENTS

| CN | 1697633 | 11/2005 |
|---|---|---|
| CN | 102670334 | 9/2012 |
| (Continued) | | |

OTHER PUBLICATIONS

"Japanese Application Serial No. 2016-535678, Office Action dated Sep. 11, 2018", (W English Translation), 7 pgs.
(Continued)

*Primary Examiner* — Si Ming Ku
(74) *Attorney, Agent, or Firm* — Schwegman Lundberg & Woessner, P.A.

(57) ABSTRACT

An anatomy simulator can include a guide body having one or more faces. The anatomy simulator can include a first simulator socket forming a recess in a first face of the one or more faces. The first simulator socket can be configured to receive a first plate. The first simulator socket can include a first base portion. The anatomy simulator can include a bore extending from the base portion of the first simulator socket to an interior of the anatomy simulator. The bore can be configured to receive an alignment mechanism. The first base portion can be angled at a first angle with respect to the first face.

19 Claims, 8 Drawing Sheets

(52) U.S. Cl.
CPC ...... *A61F 2/4684* (2013.01); *A61B 2017/568* (2013.01); *A61B 2034/102* (2016.02); *A61B 2034/105* (2016.02); *A61B 2034/108* (2016.02); *A61F 2/4014* (2013.01); *A61F 2002/30354* (2013.01); *A61F 2002/30364* (2013.01); *A61F 2002/30367* (2013.01); *A61F 2002/30378* (2013.01); *A61F 2002/30538* (2013.01)

(58) Field of Classification Search
USPC .......................................................... 606/87
See application file for complete search history.

(56) References Cited

U.S. PATENT DOCUMENTS

| | | | |
|---|---|---|---|
| 6,676,705 | B1 | 1/2004 | Wolf |
| 6,736,851 | B2 | 5/2004 | Maroney et al. |
| 6,827,740 | B1 | 12/2004 | Michelson |
| 6,887,277 | B2 | 5/2005 | Rauscher et al. |
| 6,986,790 | B2 | 1/2006 | Ball et al. |
| 7,097,663 | B1 | 8/2006 | Nicol et al. |
| 7,615,080 | B2 | 11/2009 | Ondrla |
| 7,819,923 | B2 | 10/2010 | Stone et al. |
| 8,002,838 | B2 | 8/2011 | Klotz |
| 8,052,758 | B1 | 11/2011 | Winslow |
| 8,192,497 | B2 | 6/2012 | Ondrla |
| 8,236,059 | B2 | 8/2012 | Stone et al. |
| 10,449,054 | B2 | 10/2019 | Hopkins |
| 2004/0064188 | A1* | 4/2004 | Ball ............... A61F 2/4014 623/19.11 |
| 2004/0064190 | A1 | 4/2004 | Ball et al. |
| 2004/0230197 | A1 | 11/2004 | Tornier et al. |
| 2004/0267284 | A1 | 12/2004 | Parmer et al. |
| 2007/0112430 | A1 | 5/2007 | Simmen et al. |
| 2009/0019262 | A1 | 1/2009 | Tashiro et al. |
| 2009/0125111 | A1 | 5/2009 | Copf, Jr. |
| 2009/0192621 | A1 | 7/2009 | Winslow et al. |
| 2011/0029088 | A1 | 2/2011 | Rauscher et al. |
| 2011/0106267 | A1 | 5/2011 | Grant |
| 2011/0196430 | A1 | 8/2011 | Walsh et al. |
| 2012/0046699 | A1 | 2/2012 | Jones et al. |
| 2015/0150687 | A1 | 6/2015 | Hopkins |
| 2018/0303533 | A1 | 10/2018 | Hopkins |
| 2020/0000600 | A1 | 1/2020 | Hopkins |

FOREIGN PATENT DOCUMENTS

| | | |
|---|---|---|
| CN | 1596091 | 3/2015 |
| CN | 105939682 | 9/2016 |
| DE | 10123517 | 11/2002 |
| DE | 102006002211 | 7/2007 |
| DE | 102006002211 | 9/2007 |
| EP | 0715836 | 6/1996 |
| EP | 0715836 | 10/2001 |
| EP | 1402856 | 3/2004 |
| FR | 2909860 A1 | 6/2008 |
| JP | 2004121849 | 4/2004 |
| JP | 2013521095 | 6/2013 |
| JP | 2013536022 | 9/2013 |
| JP | 2016538929 | 12/2016 |
| KR | 20130052542 A | 5/2013 |
| WO | 0182843 | 11/2001 |
| WO | 2015084791 | 6/2015 |
| WO | 2016053837 | 4/2016 |

OTHER PUBLICATIONS

"European Application Serial No. 14821928.0, Response filed Oct. 8, 2018 to Communication Pursuant to Article 94(3) EPC dated Mar. 27, 2018", 12 pgs.
"Chinese Application Serial No. 201480072332.9, Office Action dated Sep. 30, 2018", (W English Translation), 16 pgs.
"Practical Manual of Basic Standards for Social Public Safety Product Design", Office of Technical Supervision Committee of Ministry of Public Security, Standards Press of China, not in English, (Dec. 31, 1995), 12 pgs.
U.S. Appl. No. 14/557,763, Response Filed Dec. 18, 2018 to Non-Final Office Action dated Sep. 18, 2018, 13 pgs.
"Australian Application Serial No. 2014357337, First Examination Report dated Aug. 3, 2018", 5 pgs.
"U.S. Appl. No. 14/557,763, Non Final Office Action dated Sep. 18, 2018", 8 pgs.
U.S. Appl. No. 14/557,763, U.S. Pat. No. 10,449,054, filed Dec. 2, 2014, Adjustable Orthopedic Connections.
U.S. Appl. No. 16/567,755, filed Sep. 11, 2019, Adjustable Orthopedic Connections.
U.S. Appl. No. 15/956,494, filed Apr. 18, 2018, Guide Wire Alignment.
"International Application Serial No. PCT US2014 068062, Written Opinion dated Mar. 17, 2015", 6 pgs.
"International Application Serial No. PCT US2014 068062, International Search Report dated Mar. 17, 2015", 4 pgs.
"U.S. Appl. No. 14/557,763, Non Final Office Action dated Sep. 8, 2016", 12 pgs.
"U.S. Appl. No. 14/557,763, Response filed Mar. 3, 2017 to Final Office Action dated Jan. 23, 2017", 12 pgs.
"U.S. Appl. No. 14/557,763, Response filed Sep. 27, 2017 to Non Final Office Action dated Jun. 27, 2017", 12 pgs.
"International Application Serial No. PCT US2014 068062, International Preliminary Report on Patentability dated Jun. 16, 2016", 8 pgs.
"European Application Serial No. 14821928.0, Response filed Dec. 16, 2016 to Communication pursuant to Rules 161(1) and 162 EPC dated Aug. 30, 2016", 12 pgs.
"U.S. Appl. No. 14/557,763, Response Filed Apr. 11, 2018 to Final Office Action dated Jan. 11, 2018", 17 pgs.
"European Application Serial No. 14821928.0, Communication Pursuant to Article 94(3) EPC dated Mar. 27, 2018", 5 pgs.
"Chinese Application Serial No. 201480072332.9, Office Action dated Jan. 24, 2018", (W English Translation), 16 pgs.
"U.S. Appl. No. 14/557,763, Final Office Action dated Jan. 11, 2018", 11 pgs.
"U.S. Appl. No. 14/557,763, Non Final Office Action dated Jun. 27, 2017", 12 pgs.
"U.S. Appl. No. 14/557,763, Final Office Action dated Jan. 23, 2017", 13 pgs.
"U.S. Appl. No. 14/557,763, Response filed Nov. 18, 2016 to Non Final Office Action dated Sep. 8, 2016", 12 pgs.
"European Application Serial No. 18168597.5, Partial European Search Report dated Feb. 5, 2019", 10 pgs.
"European Application Serial No. 18168424.2, Extended European Search Report dated Feb. 8, 2019", 8 pgs.
"U.S. Appl. No. 15/956,494, Response filed Jun. 17, 2020 to Non Final Office Action dated Mar. 17, 2020", 15 pages.
"U.S. Appl. No. 15/956,494, Non Final Office Action dated Mar. 17, 2020", 6 pgs.
"Canadian Application Serial No. 2,932,585, Response filed Dec. 16, 2019 to Office Action dated Jun. 14, 2019", 16 pgs.
"European Application Serial No. 14821928.0, Communication Pursuant to Article 94(3) EPC dated Feb. 20, 2020", 4 pgs.
"European Application Serial No. 18168597.5, Response filed Dec. 12, 2019 to Extended European Search Report dated May 14, 2019", 16 pgs.
"Korean Application Serial No. 10-2016-7017889, Notice of Preliminary Rejection dated Dec. 19, 2019", (W/ English Translation), 10 pgs.
"Korean Application Serial No. 10-2016-7017889, Response filed Feb. 26, 2020 Notice of Preliminary Rejection dated Dec. 19, 2019", (W/ English Translation of Claims), 8 pgs.
"U.S. Appl. No. 14/557,763, Final Office Action dated Mar. 26, 2019", 11 pgs.
"U.S. Appl. No. 14/557,763, Notice of Allowability dated Aug. 14, 2019", 2 pgs.
"U.S. Appl. No. 14/557,763, Notice of Allowance dated Sep. 11, 2019", 11 pgs.

(56) References Cited

OTHER PUBLICATIONS

"U.S. Appl. No. 14/557,763, Notice of Allowance dated Jun. 10, 2019", 11 pgs.
"U.S. Appl. No. 14/557,763, Response filed May 22, 2019 to Final Office Action dated Mar. 26, 2019", 18 pgs.
"U.S. Appl. No. 15/956,494, Response Filed Dec. 3, 2019 to Restriction Requirement Filed Oct. 3, 2019", 7 pgs.
"U.S. Appl. No. 15/956,494, Restriction Requirement dated Oct. 3, 2019", 8 pgs.
"U.S. Appl. No. 16/567,755, Preliminary Amendment filed Oct. 23, 2019", 7 pgs.
"Australian Application Serial No. 2014357337, Response filed Jul. 17, 2019 to Subsequent Examiners Report dated Dec. 19, 2018", 13 pgs.
"Canadian Application Serial No. 2,932,585, Office Action dated Jun. 14, 2019", 6 pgs.
"European Application Serial No. 18168424.2, Response filed Sep. 13, 2019 to Extended European Search Report dated Feb. 8, 2019", 16 pgs.
"European Application Serial No. 18168597.5, Extended European Search Report dated May 14, 2019", 10 pgs.
"Canadian Application Serial No. 2,932,585, Office Action dated Apr. 7, 2020", 3 pages.
"Canadian Application Serial No. 2,932,585, Response filed May 12, 2020 to Office Action dated Apr. 7, 2020", 4 pages.
"European Application Serial No. 14821928.0, Response filed Jul. 1, 2020 to Communication Pursuant to Article 94(3) EPC dated Feb. 20, 2020", 28 pages.

\* cited by examiner

TOOL FOR FIXED CUSTOMISED RELATIVE ALIGNMENT OF ADJUSTABLE ORTHOPEDIC DEVICES

CLAIM OF PRIORITY

This application claims the benefit of U.S. Provisional Patent Application Ser. No. 62/488,499, filed on Apr. 21, 2017, the benefit of priority of which is claimed hereby, and which is incorporated by reference herein in its entirety.

BACKGROUND

One or more conditions (e.g., injury, bone spurs, arthritis, developmental disorder, or the like) can affect a joint (e.g., a shoulder or hip joint) and necessitate a medical procedure (e.g., total shoulder arthroplasty) to correct the one or more conditions. In an example, a surgeon conducting a total shoulder arthroplasty on a patient can place guide wires in the patient's anatomy to guide the surgeon in conducting the medical procedure.

SUMMARY

A problem to be solved can include the mal-alignment of replacement anatomy (e.g., a prosthetic device) during a medical procedure to install the replacement anatomy. Mal-alignment of replacement anatomy can be caused by a variety of factors (e.g., poor visibility of the anatomical feature undergoing the medical procedure, limited access to the anatomy, guesswork by a surgeon, or the like). In an example, a lack of ability to observe the anatomy undergoing a medical procedure can result in a mal-alignment of the replacement anatomy. Observation of the anatomy of the joint during the medical procedure can be hampered by the one or more conditions or by limited access to the joint itself (e.g., other anatomical features are blocking physical access to, or visual inspection of, the anatomy under observation).

In an example, a diminished ability to observe the anatomical feature can make it difficult to determine how to install the replacement anatomy as it relates to the anatomical feature (e.g., establish a proper orientation and position between the anatomical feature and replacement anatomy). As discussed herein, a diminished ability to observe the anatomical feature can make it difficult to determine the angular relationships (e.g., relative angles) required to be established between the anatomical feature and the replacement anatomy. A diminished ability to observe the anatomical feature can require expensive, pre-operative, medical imaging (and other pre-operative tasks) to determine a desired orientation and position of the replacement anatomy in relation to the anatomical feature. In another example, even if the ability to observe the anatomical feature is not diminished, and the preferred orientation and position of the replacement anatomy in relation to the anatomical feature can be determined during a medical procedure to install the replacement anatomy. The preferred orientation and position of the replacement anatomy in relation to the anatomical feature can be determined during the medical procedure by the use of an angular indicator.

In various embodiments of the systems and methods of the present application, an anatomy simulator, such as an alignment block having faces with variously angled sockets, can be used to facilitate alignment between medical device implant components and instrumentation components, intra-operatively or pre-operatively, as discussed below. Such an alignment block can preemptively alleviate negative effects that can be associated with mal-alignment of replacement anatomy.

The mal-alignment of the replacement anatomy can have negative effects upon the efficacy of the medical procedure. Additionally, pre-operative tasks can include fabrication of instruments that are specific to the patient's anatomical feature. The patient-specific instruments can allow for an individual (e.g., a radiologist, a surgeon, a nurse, or the like) to facilitate accurate alignment of the replacement anatomy in relation to the anatomical feature. However, patient-specific instrument fabrication can be expensive, can require specialized equipment, such as computerized tomography scanners, or can take considerable time to fabricate the model. Further, because the instrument is patient-specific, the instrument cannot be re-used in a different medical procedure.

In an example wherein a patient is undergoing a total shoulder arthroplasty procedure, the diminished ability to observe the anatomical feature of the shoulder joint can result in the mal-alignment, or improper installation, of replacement anatomy (e.g., a shoulder joint replacement apparatus). The mal-alignment of the replacement anatomy can negatively affect the durability or performance of the replacement anatomy. In an example, the mal-alignment of the replacement anatomy can cause a premature loosening of the replacement anatomy from the patient's anatomical feature or cause pain to the patient. A decrease in the durability or performance of the replacement anatomy can necessitate further medical procedures, or otherwise negatively affect the quality of life of the patient.

A solution to the aforementioned problems to be solved can include an anatomy simulator. In an example, the anatomy simulator can be an alignment block or an alignment cube. The anatomy simulator can include a guide body having one or more faces. The anatomy simulator can include a first simulator socket. The first simulator socket can include a recess in a first face of the one or more faces. The first simulator socket can be configured to receive a first plate. The first simulator socket can include a first base portion, such as within the recess. The first base portion can be angled at a first angle with respect to the first face. The anatomy simulator can include a bore. The bore can extend from the base portion of the first simulator socket to the interior of the anatomy simulator. The bore can be configured to receive an alignment mechanism.

The anatomy simulator can be used to set relative angles between the first plate and the alignment mechanism. The anatomy simulator can prevent the mal-alignment of replacement anatomy by ensuring a proper, or a desired, angular alignment between the first plate and the alignment mechanism.

Aspect 1 can include or use subject matter (such as an apparatus, a system, a device, a method, a means for performing acts, or a device readable medium including instructions that, when performed by the device, can cause the device to perform acts), such as can include or use an anatomy simulator. The anatomy simulator can include a guide body having one or more faces. The anatomy simulator can include a first simulator socket forming a recess in a first face of the one or more faces. The first simulator socket can be configured to receive a first plate. The first simulator socket can include a first base portion. The anatomy simulator can include a bore extending from the base portion of the first simulator socket to an interior of the anatomy simulator. The bore can be configured to receive an alignment mechanism. The first base portion can be angled at a first angle with respect to the first face.

Aspect 2 can include or use, or can optionally be combined with the subject matter of Aspect 1, to optionally include or use that the first plate and the alignment mechanism are configured to couple at one or more orientations and coupling the first plate with the alignment mechanism fixes the orientation of the first plate with respect to the alignment mechanism.

Aspect 3 can include or use, or can optionally be combined with the subject matter of one or any combination of Aspects 1 or 2 to optionally include or use that the first simulator socket is configured to receive the first plate such that mating the first plate with the alignment mechanism and with the first base portion establishes the first angle between the first plate and the alignment mechanism.

Aspect 4 can include or use, or can optionally be combined with the subject matter of one or any combination of Aspects 1 through 3 to optionally include or use that a portion of the alignment mechanism is quasi-spherical, and the quasi-spherical portion is configured to be received by a plate socket of the first plate.

Aspect 5 can include or use, or can optionally be combined with the subject matter of one or any combination of Aspects 1 through 4 to optionally include or use that the quasi-spherical portion includes an expansion bore, wherein the expansion bore is configured to receive an expansion pin, the expansion pin expanding the quasi-spherical portion from a first diameter to a second diameter.

Aspect 6 can include or use, or can optionally be combined with the subject matter of one or any combination of Aspects 1 through 5 to optionally include or use that expanding the quasi-spherical portion from a first diameter to a second diameter couples the first plate with the alignment mechanism and fixes the orientation of the first plate with respect to the alignment mechanism.

Aspect 7 can include or use, or can optionally be combined with the subject matter of one or any combination of Aspects 1 through 6 to optionally include or use that the first simulator socket is included in a plurality of simulator sockets and each of the one or more faces includes an individual simulator socket of the plurality of sockets.

Aspect 8 can include or use, or can optionally be combined with the subject matter of one or any combination of Aspects 1 through 7 to optionally include or use simulator indicia on the first face configured to provide alphanumerical information identifying the first angle.

Aspect 9 can include or use, or can optionally be combined with the subject matter of one or any combination of Aspects 1 through 8 to optionally include or use that the first socket includes one or more indicator portions configured to be aligned with an alignment indicia of the first plate.

Aspect 10 can include or use, or can optionally be combined with the subject matter of one or any combination of Aspects 1 through 9 to optionally include or use that the bore is configured to extend orthogonally to the first face.

Aspect 11 can include or use, or can optionally be combined with the subject matter of one or any combination of Aspects 1 through 10 to optionally include or use that the alignment mechanism is a guide wire.

Aspect 12 can include or use, or can optionally be combined with the subject matter of one or any combination of Aspects 1 through 11 to optionally include or use that the first face includes a first simulator indicia configured to provide alphanumerical information identifying the first angle. The first simulator socket can include a first indicator portion configured to receive an alignment indicia of the first plate. Aligning the alignment indicia with the first indicator portion and mating the first plate with the anatomy simulator can impart the first angle onto the first plate with respect to the first face.

Aspect 13 can include or use, or can optionally be combined with the subject matter of one or any combination of Aspects 1 through 12 to optionally include or use the first plate. The first plate can include a first plate surface configured to couple with an anatomical feature of a patient. The first plate can include a second plate surface opposite the first plate surface. The first plate can include a plate socket extending into the first plate surface. The first plate can include a bore extending from the socket to the second guide plate surface to allow a guide wire to translate through the guide plate.

Aspect 14 can include or use subject matter (such as an apparatus, a system, a device, a method, a means for performing acts, or a device readable medium including instructions that, when performed by the device, can cause the device to perform acts), such as can include or use a method for calibrating adjustable orthopaedic devices. The method can include identifying an anatomical geometry of an anatomical feature of the patient, wherein the geometry of the anatomical feature includes an anatomical axis and the anatomical geometry is at one or more angles with respect to the anatomical axis. The method can include coupling an alignment mechanism to an anatomy simulator, wherein the anatomy simulator is configured to reproduce the one or more angles with respect to the alignment mechanism. The method can include coupling a first plate with the anatomy simulator, wherein coupling the first plate with the anatomy simulator includes mating the first plate with a base portion of the anatomy simulator, wherein the mating of the first plate with the base portion establishes the first plate at the one or more angles with respect to the alignment mechanism.

Aspect 15 can include or use, or can optionally be combined with the subject matter of Aspect 14, to optionally include or use coupling an axis guide to the first plate, wherein the alignment mechanism comprises a first guide wire and coupling the axis guide includes translating the first guide wire through an axis guide wire bore of the axis guide, the axis guide wire bore configured to receive the first guide wire in a single orientation.

Aspect 16 can include or use, or can optionally be combined with the subject matter of one or any combination of Aspects 14 or 15 to optionally include or use decoupling the first plate and the axis guide as a unit from the anatomy simulator.

Aspect 17 can include or use, or can optionally be combined with the subject matter of one or any combination of Aspects 14 through 16 to optionally include or use placing a guide wire in the anatomical feature of the patient, wherein the coupling of the axis guide with the guide plate allows the guide wire to be located at the anatomical axis of the anatomical feature.

Aspect 18 can include or use, or can optionally be combined with the subject matter of one or any combination of Aspects 14 through 17 to optionally include or use mating the first plate with anatomy simulator includes mating the first plate with the alignment mechanism and establishing the first angle between the first plate and the alignment mechanism with the base portion of the anatomy simulator.

Aspect 19 can include or use, or can optionally be combined with the subject matter of one or any combination of Aspects 14 through 18 to optionally include or use that the first plate and the alignment mechanism are configured to couple at one or more orientations and coupling the first plate with the alignment mechanism fixes the orientation of the first plate with respect to the alignment mechanism.

Aspect 20 can include or use, or can optionally be combined with the subject matter of one or any combination of Aspects 14 through 19 to optionally include or use that a portion of the alignment mechanism is quasi-spherical, and the quasi-spherical portion is configured to be received by a plate socket of the first plate.

Aspect 21 can include or use, or can optionally be combined with the subject matter of one or any combination of Aspects 14 through 20 to optionally include or use expanding an expansion bore of the quasi-spherical portion, wherein the expansion bore is configured to receive an expansion pin, the expansion pin expanding the quasi-spherical portion from a first diameter to a second diameter.

Aspect 22 can include or use, or can optionally be combined with the subject matter of one or any combination of Aspects 14 through 21 to optionally include or use identifying an anatomical geometry of an anatomical feature of the patient includes determining the one or more angles of the anatomical geometry with respect to the anatomical axis.

Each of these non-limiting examples can stand on its own, or can be combined in various permutations or combinations with one or more of the other examples.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
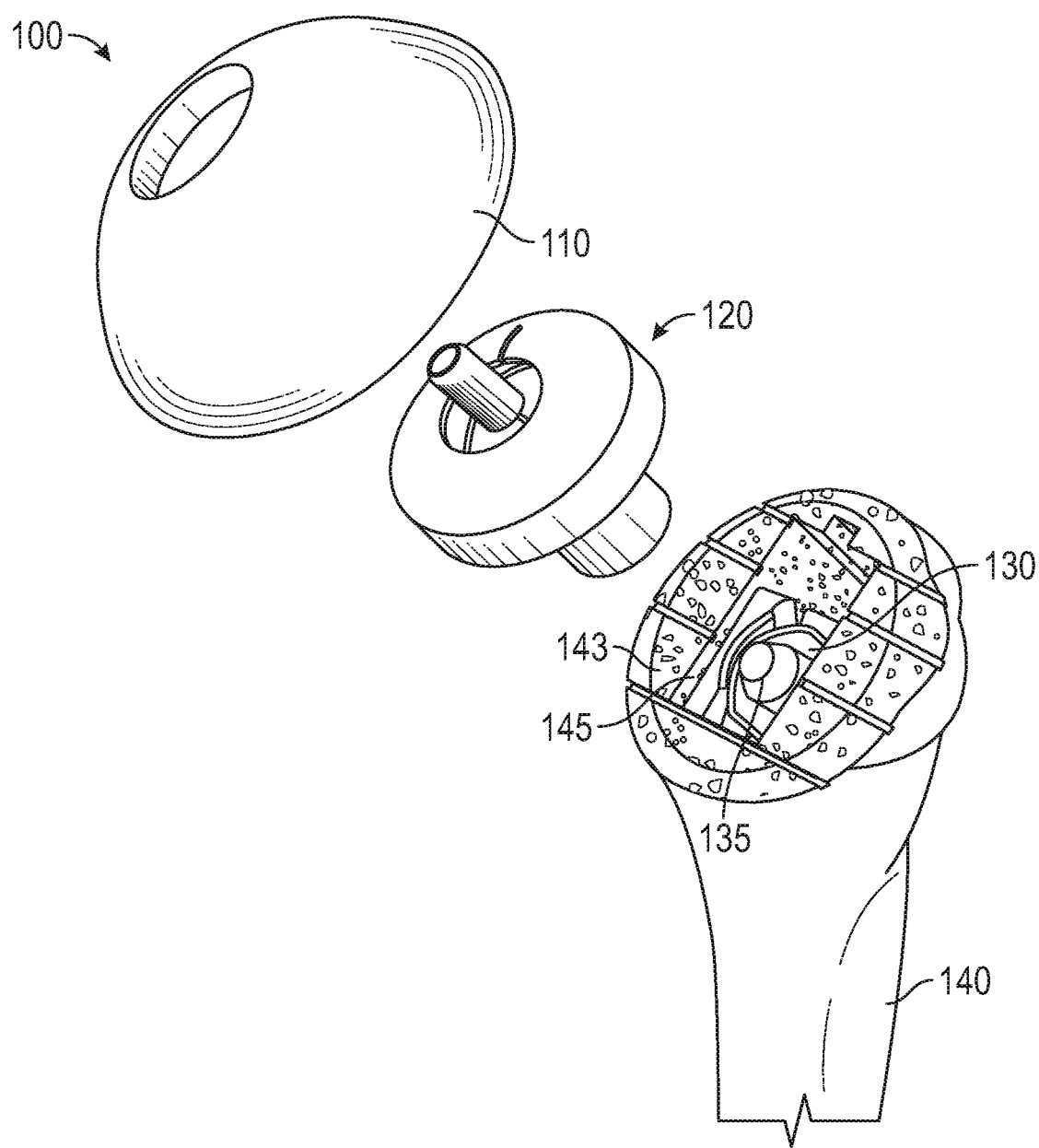
FIG. 1 is a perspective view of an adjustable orthopedic system including a head, an adjuster, a stem, and a humerus.

As discussed herein, a diminished ability to observe an anatomical feature of a patient can make it difficult to determine intra-operatively how to install the adjustable orthopedic system 100 (FIG. 1) as it relates to the anatomical feature, e.g., establish a proper orientation and position between the anatomical feature and replacement anatomy. The preferred orientation and position of the replacement anatomy (e.g., a head 110, an adjuster 120 and a stem 130) in relation to the anatomy can be determined during the medical procedure by the use of an angular indicator (e.g., angular indicator 410 of FIG. 4 or angular indicator 510 of FIG. 5).

Also, a diminished ability to observe an anatomical feature of a patient can make it difficult to determine how to assemble and install the adjustable orthopedic system 900 (see FIG. 9), e.g., establish a proper orientation between components of an instrumentation systems. The preferred orientation and position of components of the orthopedic system 900 (e.g., guide plate 951 and the axis guide 952) can be determined pre-operatively using medical imaging.

An anatomical simulator (e.g., the alignment block 630 of FIGS. 6 and 7, or the alignment cube 830 of FIG. 8) can be used to intraoperatively to configure the relative angles between the anatomical feature and the replacement anatomy. The anatomical simulator can be used to set the relative angles of components of the replacement anatomy (e.g., between the head 220 and the ball taper 230 of the adjustor 120 of FIGS. 1-3).

Figure 8:
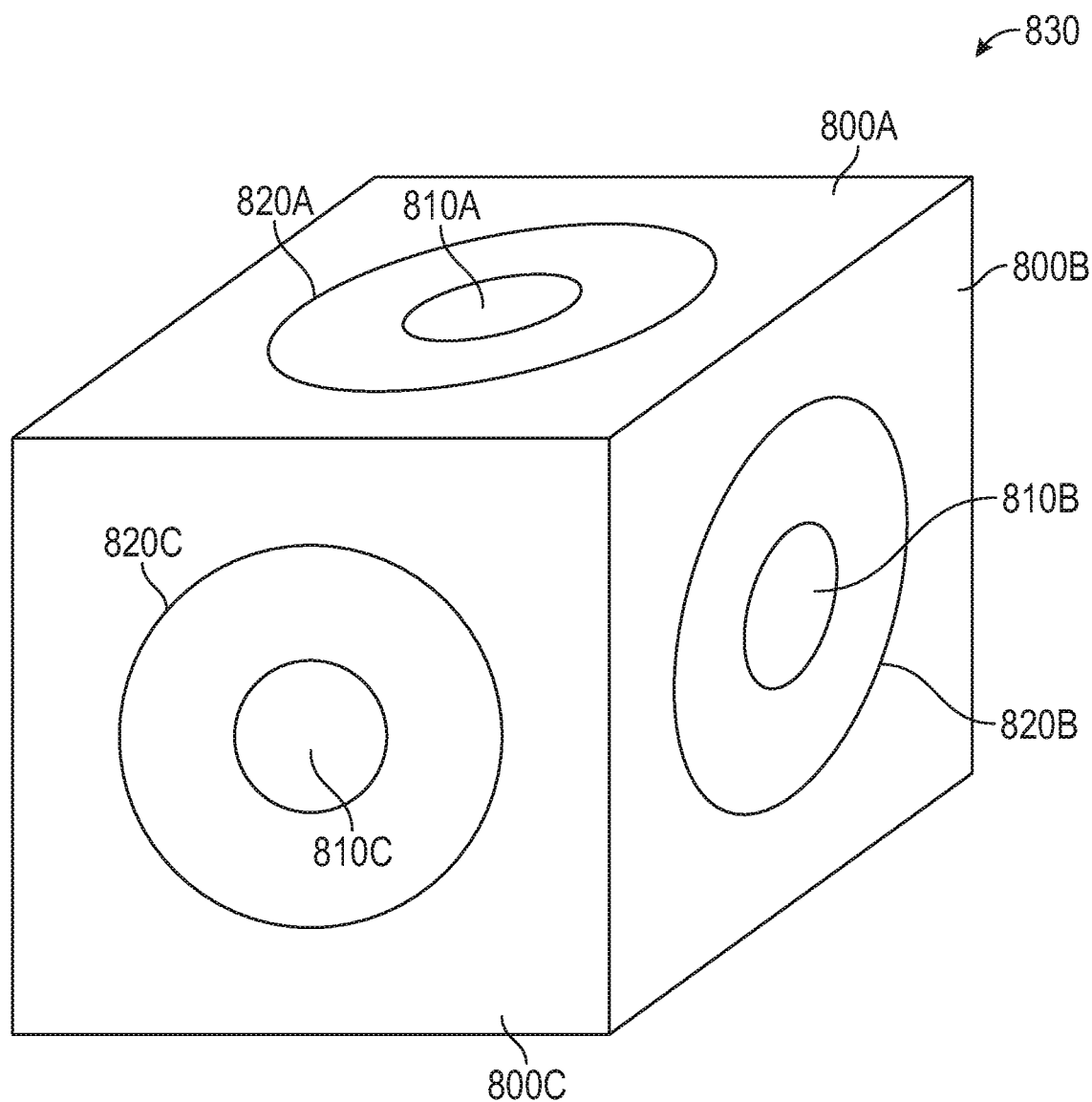
FIG. 8 is a perspective view of an alignment cube for use with the adjustable orthopedic system of FIG. 1.
Figure 9:
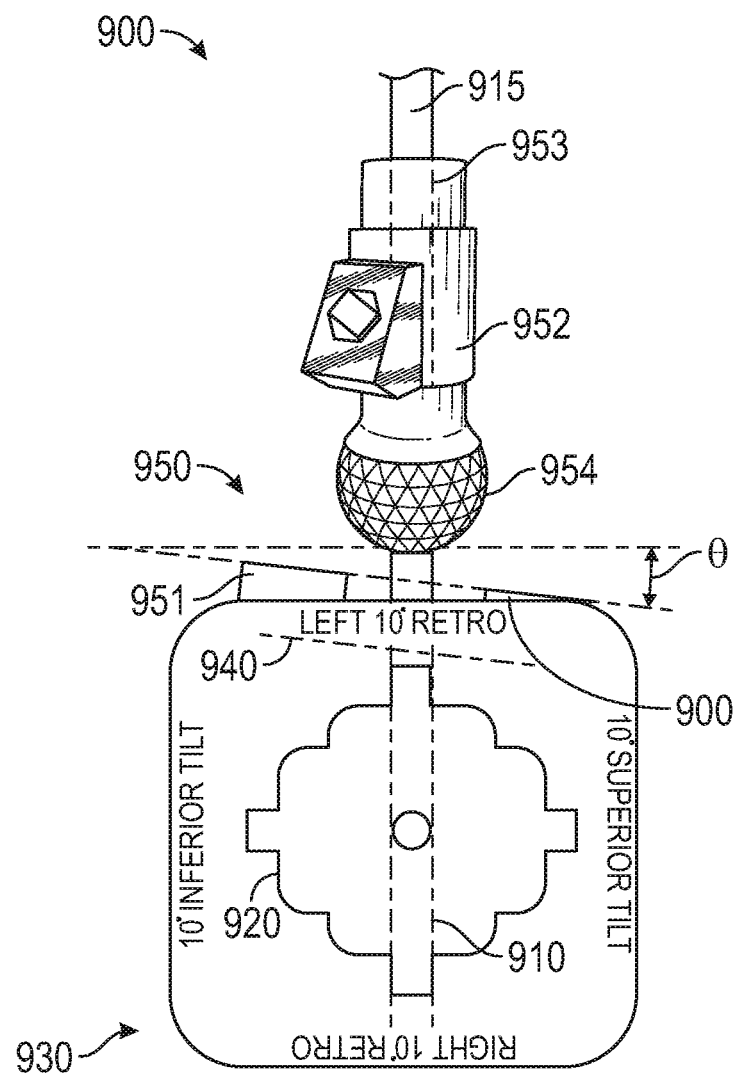
FIG. 9 a side view of another example of an adjustable orthopedic system including another alignment cube and an alignment unit.
Figure 10:
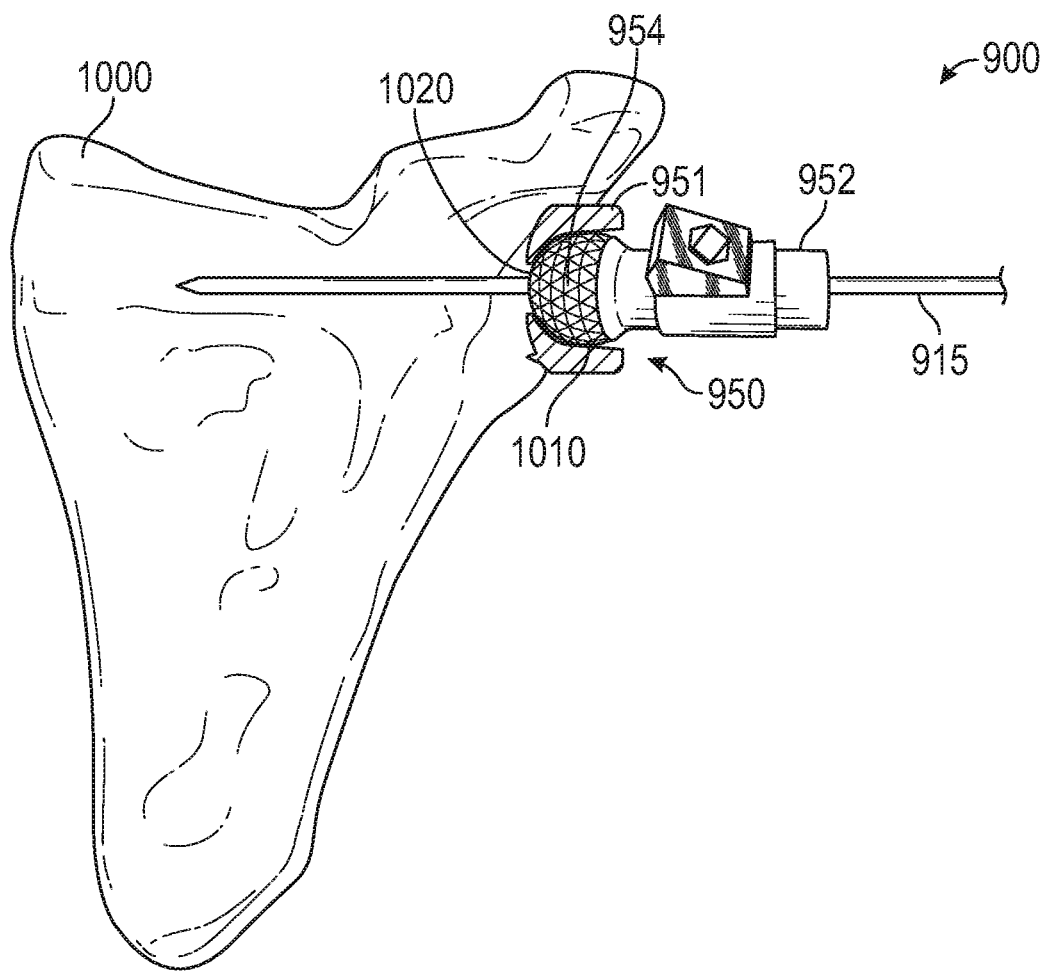
FIG. 10 is a posterior view of an example of a adjustable orthopedic system of FIG. 9 showing the alignment unit coupled with an anatomical feature.

An anatomical simulator (e.g., alignment cube 930 of FIG. 9) can be used to pre-operatively configure the relative angles between the guide plate 951 and the axis guide 952 of FIGS. 9 and 10. In an example, the anatomy simulator can be an alignment block (e.g., the alignment block 630 of FIGS. 6 and 7) or an alignment cube (e.g., the alignment cube 830 of FIG. 8, or the alignment cube 930 of FIG. 9). The anatomy simulator can include a guide body having one or more faces with angled sockets, as discussed below. The anatomy simulator, such as an alignment cube, can be used to set relative angles between various components. The anatomy simulator can prevent the mal-alignment of replacement anatomy or surgical instrumentation by ensuring a proper, or a preferred, angular alignment between components.

FIG. 1 is a perspective view of an adjustable orthopedic system 100 including a head 110, an adjuster 120, a stem 130, and a humerus 140. The head 110 can be configured to replicate a portion of an anatomical feature of a patient. The head 110 can have a circular cross section. The head 110 can have a round, or oval cross section. The head 110 can have a non-uniform cross section. The head 110 can replicate a portion of a humeral head. The head 110 can replicate a portion of a femoral head. In an example, a patient's humeral head is misshapen (e.g., due to injury, disease, malformation, or the like). As shown in FIG. 1, a portion of the humeral head can be removed from a remaining portion of the humerus. The head 110 can be coupled to the remaining portion of the humerus. The head 110 can provide an improved surface for the humerus to mate with the scapula, such as by providing a smooth, consistent surface free from protrusions (e.g., malformations) or debris (e.g., bone spurs).

The head 110 shown in FIG. 1 can be a provisional head used for determining the correct size and shape of a head 110 to be permanently coupled with the anatomical feature. As previously discussed, a portion of the anatomical feature can be removed. The dimensions and orientation of the anatomical feature can vary from a first patient to a second patient. Use of the provisional head can allow for a medical practitioner to determine the correct configuration of the head 110 to permanently couple with the anatomical feature of the patient. The provisional head can include indicia (e.g., markings) that indicate what type (e.g., circular or non-circular cross section) and/or size of head 110 can be permanently coupled to the anatomical feature.

The head 110 can be coupled to the adjustor 120. The head 110 can be coupled to the adjustor 120 in one or more orientations. The coupling of the head 110 to the adjustor 120 can be referred to as positionable mating of the head 119 with the adjustor 120. Positionable mating of the head 110 with the adjustor 120 can also be referred to as fixable positioning. Fixable positioning of the adjustor 120 can include when the position, or orientation, of the components of the adjustor 120 remain fixed, or unchanged, once the position or orientation of those components has been established or set, such as by a surgeon. As discussed herein, fixable positioning can be achieved by an interference fit between the components of the adjustor 120. The adjustor 120 can be configured to allow fixable positioning of the adjustor 120 components to allow for the adjustor 120 to adapt to variations in an anatomical feature of a patient.

As shown in FIG. 1, a portion of the humerus 140 has been cut away and removed (e.g., the humerus 140 has been resected). The angle of the cut can vary upon needs of a patient, such as by accounting for malformation or damage to the portion of the humerus 140 being removed. The resected portion of the humerus 140 can have a flat face 143. The fixable positioning of the adjustor 120 can allow for a wide range of angular relationships between the head 110, the stem 130, and the humerus 140 to be achieved. Stated another way, the adjustor 120 allows for non-patient-specific components (e.g., the head 110 and the stem 130) to be configured into a patient-specific orientation or relationship with respect to the humerus 140. Although the humerus 140 is the anatomical feature under discussion, the devices and methods described herein can be used with various anatomies, such as hips, shoulders, and the like.

The stem 130 can be configured to couple with the humerus 140. The stem 130 can couple with a medullary cavity of the humerus 140. A cavity 145 (e.g., the medullary cavity) can be made in the humerus 140. The cavity 145 can be configured to receive the stem 130. The cavity 145 can be located at the portion of the humerus 140 that has been cut away and removed. The cavity 145 can extend into the interior of the humerus 140. The stem 130 can have a rough exterior surface for increasing the coefficient of friction of the exterior surface, thereby improving the coupling of the stem 130 with the humerus 140. The stem 130 can be coupled to the humerus 140 with an adhesive (e.g., glue, epoxy, cement, or the like). The volume of the cavity 145 surrounding the stem 130 can be filled with the adhesive. Coupling the stem 130 to the humerus 140 with an adhesive can improve the strength and resiliency of the coupling of the stem 130 to the humerus 140. Coupling the stem 130 with the humerus 140 can allow for other structures, such as the adjuster 120, to be coupled to the stem 130 and thereby to the humerus 140. The stem 130 can have a coupler 135 configured to allow the adjustor 120 to couple and decouple from the stem 130. The adjustor 120 can be configured to include an adjustor coupling feature that corresponds to the coupler 130, such that the adjustor 120 can couple and decouple from the stem 130.

Figure 2:
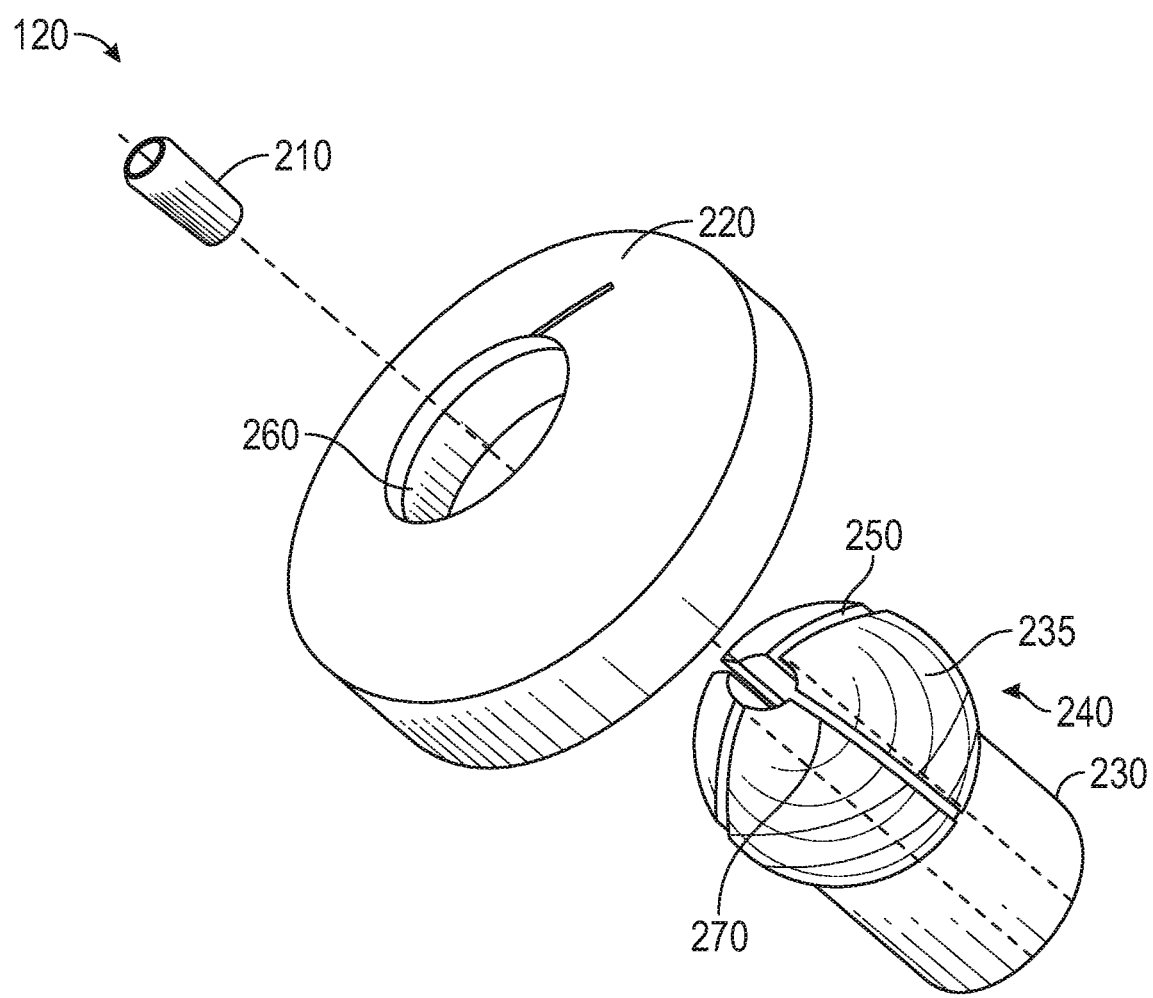
FIG. 2 is a perspective view of the adjuster of FIG. 1 including an expansion pin, a dome, and a ball-taper.

FIG. 2 is a perspective view of the adjuster 120 of FIG. 1 including an expansion pin 210, a dome 220, and a ball-taper 230. The dome 220 can be configured to be orientated in a plurality of positions with respect to the ball-taper 230. Stated another way, the dome 220 has numerous degrees of freedom and can be positioned at a variety of angles with respect to the ball-taper 230. As discussed herein, the adjustor 120 can be configured to allow the fixable positioning of the components of the adjustor 120. Stated another way, the adjustor 120 can be configured to allow for the orientation of the dome 220 relative to the ball-taper 230 to be fixed once the orientation has been established.

The dome 220 can be a first plate. The dome 220 can include a dome socket 260. The dome socket 260 can be configured to receive a head 240 of the ball-taper 230. The dome socket 260 can be configured to positionably mate with the head 240 of the ball-taper 230. In an example, the head 240 of the ball-taper 230 can be quasi-spherical and the dome socket 260 can be sized and shaped such that the dome 220 is loosely coupled (e.g., able to freely be reoriented) with the ball-taper 230.

The ball-taper 230 can be an alignment mechanism. The ball-taper 230 can include one or more expansion slots 250. The one or more expansion slots 250 can be configured to expand in response to an applied force. Expansion of the one or more expansion slots 250 can change (e.g., increase or decrease) the dimensions of the ball-taper 230. Expansion of the one or more expansion slots 250 can change the dimensions of the head 240. Expansion of the one or more expansion slots 250 can change the head 240 from a first diameter to a second larger diameter.

The expansion of the one or more expansion slots 250 can be achieved by allowing a petal 235 to deflect. The adjustor 120 can include one or more petals.

The ball-taper 230 can include an expansion bore 270. The expansion bore 270 can be included in the head 240. The expansion bore 270 can have a circular cross section. The expansion bore 270 can be tapered. The one or more expansion slots 250 can extend from the exterior of the ball-taper 230 to the expansion bore 270. The expansion bore 270 can be configured to receive the expansion pin 210. The one or more petals can define the expansion bore 270.

The expansion pin 210 can be a cylinder with a constant diameter. The expansion pin 210 can include a cone portion (e.g., the diameter of the expansion pin 210 changes linearly along a portion of a length of the expansion pin 210). The expansion pin 210 and expansion bore 270 can be configured such that when the expansion pin 210 is translated into the expansion bore 270, the one or more petals deflect. The deflection of the one or more petals can cause the expansion slots 270 to expand. The one or more expansion slots 270 can expand outward (e.g., toward the exterior) from the ball-taper 230.

In an example, the expansion pin 210 can be tapered and can be translated into the expansion bore 270. As the expansion pin 210 is translated into the expansion bore 270, a portion of the expansion pin 210 engages with, and acts upon, the expansion bore 270. The expansion bore 210 can be a smooth bore with a consistent diameter. The one or more expansion slots 240 can allow for the diameter of the expansion bore 270 to change.

The one or more expansion slots 240 can allow for the diameter of the expansion bore 270 to change as the expansion pin 210 is translated within the expansion bore 270. As the expansion pin 210 is translated deeper into the expansion bore 270, the larger diameter portion of the expansion pin 210 begins engaging with the expansion bore 270. Continued translation of the expansion pin 210 within the expansion bore 270 forces the diameter of the expansion bore 270 to increase and match the largest diameter portion of the expansion pin 210 that is engaging with the expansion bore 270. Expansion of the expansion bore 270 can be accomplished by tapering the expansion pin 210, the expansion bore 270, or tapering both the expansion pin 210 and the expansion bore 270. Expansion of the expansion bore 270 can cause the one or more petals to deflect. Other configurations are possible for expanding the expansion bore 270, such as by using fasteners, electo-mechanical components, hydraulic components, or the like.

Expanding the expansion bore 270 can allow for the dome 220 to positionably mate with the ball-taper 230. Postionable mating can occur through an interference fit between the dome 220 and the ball-taper 230. The expansion bore 270 can be expanded by the expansion pin 220, thereby deflecting the one or more expansion slots 240 outward. The outward deflection of the expansion slots 240 changes the diameter of the head 240 from a first diameter to a second diameter. The dome socket 260 can be configured to have substantially the same shape as the head 240 of the ball-taper 230. The dome socket can have the second diameter. Expanding the expansion bore 270 can force the head 240 to engage with the dome socket 260. The expansion bore 270 can be expanded such that the dome 220 and the ball-taper 230 become positionably mated. Further translation of the expansion pin 210 within the expansion bore 270 can generate greater frictional forces between the head 220 and the dome socket 260, thereby tightening the coupling between the dome 220 and the ball-taper 230. Stated another way, translating the expansion pin 210 deeper into the expansion bore 270 can increase an amount of force necessary to reorient the dome 220 with respect to the ball-taper 230.

Assembly of the adjustor 120 can be accomplished by mating the dome 220 with the ball-taper 230. As described herein, the orientation of the dome 220 with respect to the ball-taper 230 can be established by using an alignment block (e.g., the alignment block 630 of FIG. 6) or an alignment cube (e.g., the alignment cube 830 or 930 of FIG. 8 or 9, respectively). The alignment block or alignment cube can establish the relative angles between the dome 220 and the ball-taper 230. The dome 220 can include a through-hole configured to allow the expansion pin 210 to translate through the through-hole. The through-hole in the dome 220 can be configured to allow the expansion pin 210 to translate through the dome 220 and into the expansion bore 270 of the ball-taper 230. The expansion pin 210 can be inserted into the expansion bore 270 once the orientation of the dome 220 with respect to the ball-taper 230 has been established. As discussed herein, the expansion pin 210 can fix the orientation of the dome 220 with respect to the ball-taper 230 by forcing the petals 235 to push against dome socket 260.

Figure 3:
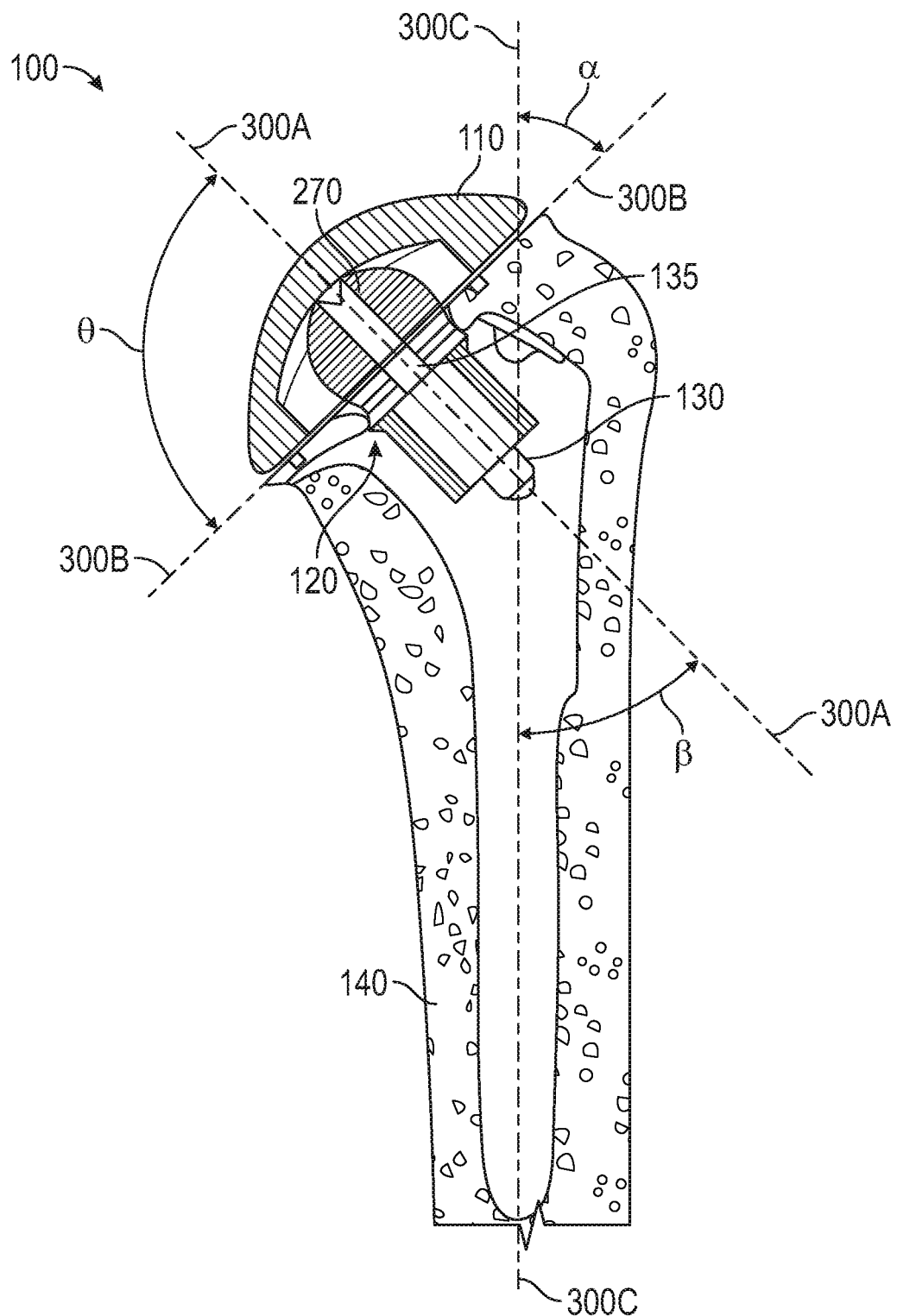
FIG. 3 is a cross-sectional view of the adjustable orthopedic system of FIG. 1.

FIG. 3 is a cross-sectional view of the adjustable orthopedic system 100 of FIG. 1. The adjustable orthopedic system 100 can include the head 110, the adjustor 120, the stem 130, and the humerus 140. The humerus 140 can include a first axis 300A, a second axis 300B, and a third axis 300C. The first axis 300A, second axis 300B, and the third axis 300C can be referred to collectively as the axes 300A, 300B, and 300C. The first axis 300A and the second axis 300B can be offset at a first angle α. The second axis 300B and the third axis 300C can be offset at a second angle β. The first axis 300A and the third axis 300C can be offset at a third angle Θ. The humerus 140 can have a fourth axis (e.g., the fourth axis 500 of FIG. 5). The fourth axis can extend orthogonally to the first and second axis 300A and 300B. Stated another way, the fourth axis can extend perpendicular to the sheet.

As discussed herein, a portion of an anatomical feature can be cut and removed (e.g., resected). As shown in FIG. 3, axis 300C extends longitudinally through the humerus 140. A portion of the humerus 140 (e.g., a portion of the head) has been resected. The resected portion of the humerus 140 can have a flat face (e.g., the flat face 143 of FIG. 1). The axis 300B can be collinear with the face of the resected portion. The face can be oriented at the angle α with respect to the axis 300C. The adjustor 120 can articulate to match the angle α. Stated another way, the adjustor 120 can be configured to be orientated at the angle α with respect to the axis 300C. As shown in FIG. 3, the axis 300A can be a longitudinal axis of the stem 130. The stem 130 can be orientated at the angle α such that the coupler 135 is orthogonal to the face. In an example, the stem 130 is oriented at an angle different than α. The adjustor 120 can be configured to couple with the stem 130 such that the head 110 will be parallel (e.g., able to mate with substantially no gaps) to the flat face of the humerus 140. Stated another way, the adjustor 120 can be configured to compensate for angular misalignment between the head 110 and the stem 130. The adjustor 120 can compensate for angular misalignment between the stem 130 and the head 110 by articulating at the angle Θ. The adjustor 120 can be configured to articulate in the direction of the second axis 300B.

Figure 5:
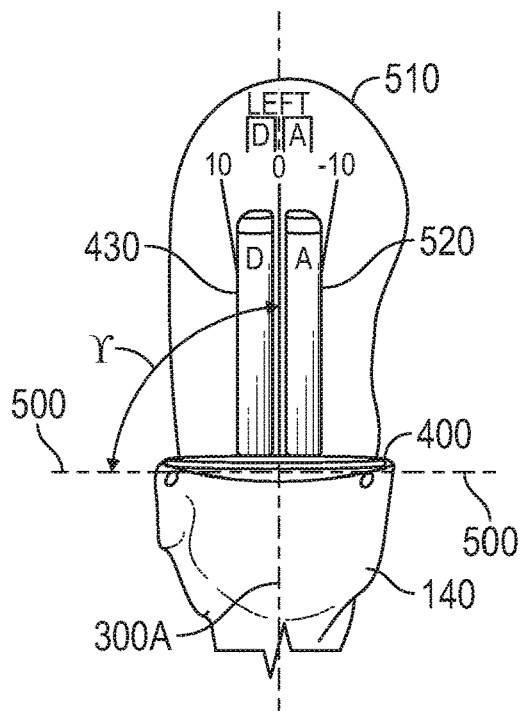
FIG. 5 is a superior view of the humerus and the angular indicator of FIG. 4 and a second angular identification card for use with the adjustable orthopedic system of FIG. 1.

As discussed herein, the humerus 140 can have a fourth axis (e.g., the fourth axis 500 of FIG. 5). The fourth axis can extend orthogonally to the first and second axis 300A and 300B. Stated another way, the fourth axis can extend perpendicular to the plane of FIG. 3. The adjustor 120 can be configured to articulate in the direction of the fourth axis 500. Articulating in the direction of the fourth axis can compensate for angular misalignment between the stem 130 and the head 110, such as when the flat face has a slope in the direction of the fourth axis.

Figure 4:
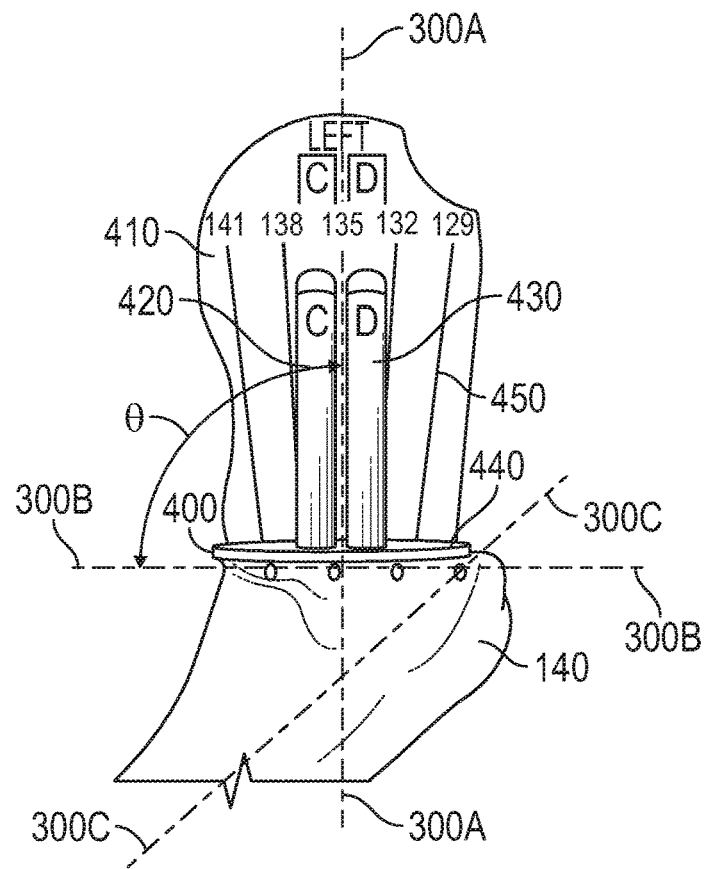
FIG. 4 is an anterior view of a humerus, and an angular indicator and a first angular identification card for use with the adjustable orthopedic system of FIG. 1.

FIG. 4 is an anterior view of a humerus 140, and an angular indicator 400 and a first angular identification card 410 for use with the adjustable orthopedic system 100 of FIG. 1. The angular indicator 400 can include a first finger 420, a second finger 430, and a base plate 440. The first finger 420 and the second finger 430 can extend orthogonally from the base plate 440. The angular identification card 410 can be mated with a reference surface (e.g., the base plate 440 or the face 143 of FIG. 1). The angular identification card 410 can be located proximate to the angular indicator 400 such that an angular indicia, such as an angular indicia 450, to be seen between the first and second fingers 420 and 430.

The base plate 440 can include an indicator coupling feature configured to couple and decouple with a coupler (e.g., the coupler 135 of FIG. 1) of the stem 130, such that the angular indicator 400 can couple and decouple from the stem 130. The first and second fingers 420 and 430 can be parallel in relation to each other. The first and second fingers 420 and 430 can be spaced apart at a first distance. Spacing the first and second fingers 420 and 430 at the first distance can allow for the angular indicia 450 of the first angular identification card 410 to be seen between the first and second fingers 420 and 430.

In an example, the first and second fingers 420 and 430 can provide an indication of the angle Θ between the first axis 300A and the second axis 300B. The angular indicia 450 can provide an indication of the angle Θ. The first and second fingers 420 and 430 can be configured to provide an indication of an angle between any combination of the first axis 300A, second axis 300B, third axis 300C, or the fourth axis (e.g., the fourth axis 500 of FIG. 5). The first and second fingers 420 and 430 can include finger indicia. The first angular identification card 410 can include card indicia that correspond to the finger indicia to ensure that the first angular identification card is being used with the first and second fingers 420 and 430 and thereby provide the correct angle Θ.

FIG. 5 is a superior view of the humerus 140 and the angular indicator 400 of FIG. 4 and a second angular identification card 510 for use with the adjustable orthopedic system 100 of FIG. 1. The angular indicator 400 can include the second finger 430 and a third finger 520. Inclusion of the third finger 520 can allow for the angular relationship of multiple axis (e.g., the first axis 300A, second axis 300B, third axis 300C, or a fourth axis 500) to be determined without decoupling the angular indicator 400 from the stem 130. The second and third fingers 430 and 520 can allow for an angle γ between the first axis 300A and the fourth axis 500 to be determined.

Figure 6:
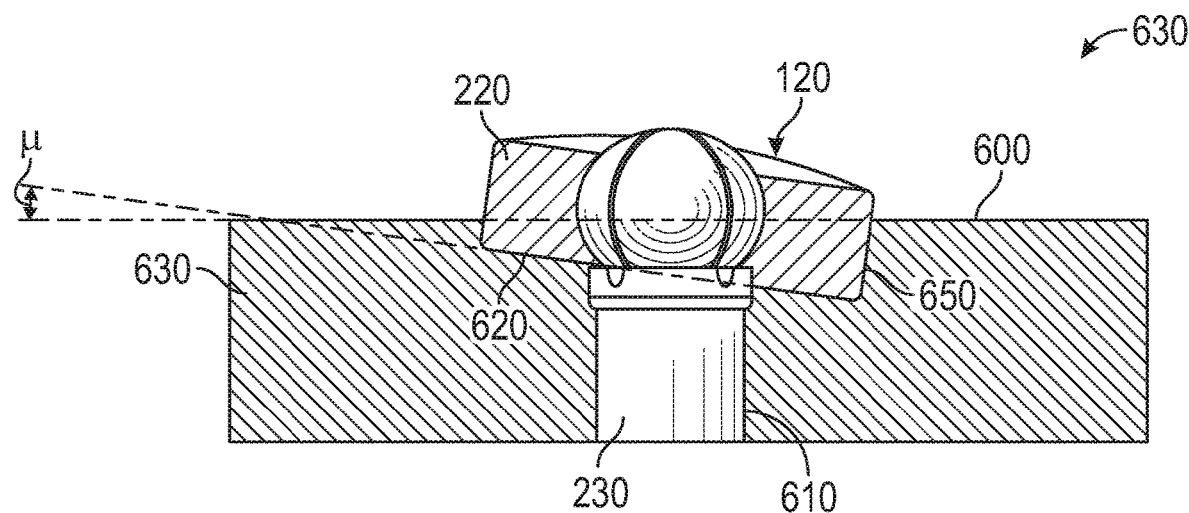
FIG. 6 is a schematic view of an alignment block mated with the adjustor for use with the adjustable orthopedic system of claim 1.

FIG. 6 is a schematic view of an alignment block 630 mated with the adjustor for use with the adjustable orthopedic system 100 of claim 1. The alignment block 630 can be an anatomy simulator. The alignment block 630 can include a body. The alignment block 630 can be used to set relative angles between a dome (e.g., the dome 220 of FIG. 1) and a ball taper (e.g., the ball-taper 230 of FIG. 1). The alignment block 630 can be used to set the angles α, β, Θ, and γ. In an example, the alignment block 630 can include a face 600, an alignment bore 610, a base portion 620, one or more block indicia 640A, 640B, 640C, and 640D, a slot 650.

In an example, the face 600 can include the slot 650. The slot 650 can include the base portion 620. The slot 650 can be configured to receive the dome. The slot 650 can be configured to receive the dome in a plurality of orientations. The reception of the dome by the slot 650 can mate the dome with the base portion 620 of the slot 650. The alignment bore 610 can extend from the face 600 to another face located on the opposite side of the alignment block 630. The alignment bore 610 can be configured to receive a ball taper (not shown) in one or more orientations. As shown in FIG. 6, the alignment bore 610 can be configured such that the ball taper can be received by the alignment bore 610 in four orientations. The alignment bore 610 can include a first lobe 660A, a second lobe 660B, a third lobe 660C, and a fourth lobe 660D. Additional or fewer lobes can be included in the alignment bore 610.

In an example, the base portion 620 of the slot 650 can be configured as an inclined plane. Stated another way, the bottom (e.g., the base portion 620) of the slot 650 can be angled at an angle μ (e.g., the angle μ of FIG. 7) such that a first distance from a first side of the slot 650 to the face 600 can be different than a second distance from the bottom of a second side of the slot 650 to the face 600. Stated yet another way, the depth of the slot 650 relative to the face 600 can vary over the area of the slot 650. The base portion 620 of the slot 650 can be configured to include a plurality of inclined planes. The inclined plane can have an angular slope from a first end of the inclined plane to a second end of the inclined plane. The one or more block indicia 640A, 640B, 640C, and 640D can be used to identify the angular slope of the inclined plane. The one or more block indicia 640A, 640B, 640C, and 640D can respectively be aligned with the first, second, third, and fourth lobes 660A, 660B, 660C, and 660D. The angle μ can equal the angles α, β, Θ, and γ.

Figure 7:
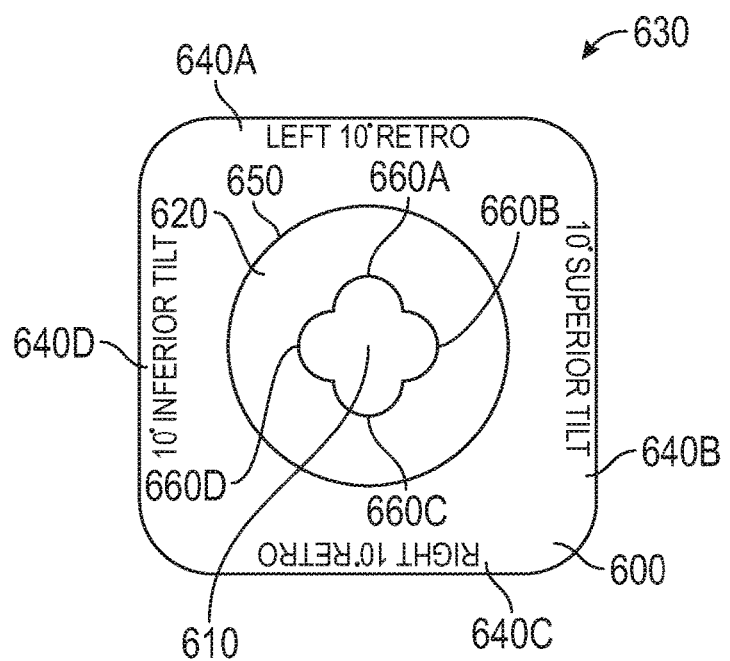
FIG. 7 is a top view of the alignment block of FIG. 6.

FIG. 7 is a top view of the alignment block of FIG. 6. The ball-taper 230 can include lobes (not shown) configured to correspond with the first, second, third, and fourth lobes 660A, 660B, 660C, and 660D. The lobes of the ball-taper 230 can correspond with the first, second, third, and fourth 230 lobes 660A, 660B, 660C, and 660D such that the ball-taper 230 is received by the alignment bore 610 in one of four orientations, although additional or fewer orientations are possible. The first, second, third, and fourth lobes 660A, 660B, 660C, and 660D can be used to orientate the ball-taper 230 with respect to the alignment block 630. The ball-taper 230 can include an alignment indicia (not shown) used for maintaining the orientation of the ball taper. For example, the alignment indicia can be a colored portion of the ball-taper 230 that allows an individual to consistently orientate the ball-taper 230. The alignment indicia can be other markings on the ball tapper 230 that allows for an individual to consistently orientate the ball-taper 230. The alignment indicia can be used to orientate the ball-taper 230 with respect to the stem 130 (shown in FIGS. 1 and 3) such that the orientation imparted to the adjustor 120 can be transferred to the adjustable orthopedic system 100.

The alignment indicia (not shown) can be aligned with the first lobe 660A. In an example, aligning the alignment indicia with the first lobe 660A and placing the alignment unit 120 within the slot 650 (e.g., mating the dome 220 with the slot 650, and the ball-taper 230 with the alignment bore 610) results in the dome 220 being angled at a 10 degree angle relative to the face 600 of the alignment block 630 (and the ball-taper 230). In another example, aligning the alignment indicia with the second lobe 660B and placing the adjustor 120 within the slot 650 results in the dome 220 being angled at a 10 degree angle relative to the face 600 of the alignment block 630 (and the ball-taper 230). However, by aligning the alignment indicia with the second lobe 660B instead of the first lobe 660A, the 10 degree angle relative to the face 600 will be reoriented into a different orientation with respect to the alignment block 630 (and the ball-taper 230). Stated another way, aligning the alignment indicia with the second lobe 660B instead of the first lobe 660A can allow for the dome 220 to be oriented at a 10 degree angle with respect to the face 600, but the direction of the tilt will differ depending upon the orientation of the adjustor 120 within the slot 650. Once the relative angles between the dome 220 and the ball-taper 230 have been established, the expansion pin 210 (shown in FIG. 2) can be driven into the expansion bore 270 (shown in FIG. 2), thereby temporarily fixing the position of the dome 220 with respect to the ball-taper 230.

In an example, the alignment indicia (not shown) can be positioned in the superior direction when the adjustor 120 is coupled with the stem 130 (shown in FIGS. 1 and 3). The base portion 620 of the alignment block 630 can be at an angle with respect to the face 600. In the example of FIG. 7, the base portion 620 can slope downward at a 10 degree angle (e.g., the angle μ is equal to 10 degrees) from left to right (e.g., the right side of the base portion 620 will have a greater depth than the left side of the base portion 620). In an example, a medical practitioner is operating on a patient's left-side scapula. Placing the adjustor 120 within the slot 650 such that the alignment indicia (not shown) is aligned with the first lobe 660A, can result in the dome 220 having 10 degrees of retroversion tilt when coupled to the left-side scapula. However, if the dome 220 were coupled to a right-side scapula, the dome 220 would have 10 degrees of anteversion tilt. Furthermore, if the adjustor 120 were positioned so that the alignment indicia is aligned with third lobe 660C, the adjustor 120 would be configured to provide 10 degrees retroversion tilt for a right shoulder.

Placing the adjustor 120 within the slot 650 such that the alignment indicia is aligned with the second lobe 660B, can result in the dome 220 (with respect to the ball-taper 230) having 10 degrees of superior tilt when coupled to the left-side scapula. Placing the adjustor 120 within the slot 650 such that the alignment indicia is aligned with the fourth lobe 660D can result in the dome 220 having 10 degrees of inferior tilt (with respect to the ball-taper 230) when coupled to the left-side scapula. Because the inferior/superior relationship is unaffected by which side of the body an anatomical feature is located on, the dome 220 can have 10 degrees of inferior tilt or superior tilt when coupled to a right-side, or a left-side scapula when using fourth and second lobes 660D and 660B, respectively.

The positionable mating of the ball-taper 230 and the dome 220 can allow for the position, or orientation, of the ball-taper 230 relative to the dome 220 to remain temporarily fixed, or unchanged, once the position or orientation has been established or set, such as by a surgeon using the alignment block 630. The ball-taper 230 and the dome 220 can have more than one relative angle set (e.g., the angles α, β, Θ, and γ). In an example, the angle α can be in a first plane. The ball-taper 230 and the dome 220 can be set at a second angle β along a second plane. The first plane can be different than the second plane. The first plane can be orthogonal to the second plane. Additional relative angles and planes are capable of being used with the ball-taper 230 and the dome 220. The mated (e.g., coupled) ball-taper 230 and the dome 220 can be removed (e.g., decoupled) from the alignment block 630 as the adjustor 120. The adjustor 120 can maintain the relative angles between the ball-taper 230 and the dome 220 that were set using the alignment block 630.

An individual (e.g., a radiologist, a surgeon, a nurse, or the like) can determine the anatomical geometry of a patient by performing medical imaging on an anatomical feature of the patient. In an example, x-ray images can be taken of the anatomical feature in various reference plan views (e.g., superior, anterior, medial, or the like). The anatomical geometry, such as the angular relationship of the anatomical feature with respect to another anatomical feature or the reference plan views, can be determined by the individual from the x-rays. The individual can use the alignment block 630 to establish the relative angles between the dome 220 and the ball-taper 230. The relative angles can be substantially similar (e.g., within 10 degrees) to the angular relationship determined from the x-rays. Use of x-rays and the alignment block 630 can eliminate the need for more expensive forms of medical imaging. Use of x-rays and the alignment block 630 can eliminate the need for fabricating a patient specific model of the anatomical feature. Fabrication of the patient specific model can be expensive. Additionally, the alignment block 630 can be included in a set of alignment blocks. The set of alignment blocks can provide a variety of combinations of superior, inferior, anteversion and retroversion settings.

FIG. 8 is a perspective view of an alignment cube 830 for use with the adjustable orthopedic system 100 of FIG. 1. The alignment cube 830 can be an anatomy simulator. The alignment cube 830 can be similar to the alignment block 630, such as including similar features, but providing additional configuration options. The alignment cube 830 can include a first face 800A, a second face 800B, a third face 800C, a first alignment bore 810A, a second alignment bore 810B, a third alignment bore 810C, a first slot 820A, a second slot 820B, and a third slot 830C. The face 600 of FIGS. 6 and 7 can be one of six faces of the alignment cube 830. Stated another way, the first face 800A can be the alignment block 600 of FIGS. 6 and 7.

The alignment cube 830 can provide additional combinations of superior, inferior, anteversion and retroversion settings than the alignment block 630. The alignment cube 830 can have different combinations of superior, inferior, anteversion and retroversion settings than the alignment block 630. In an example, the first slot 820A can impart an angle to the dome 220 relative to the first face 800A. The angle can vary depending upon what face of the alignment cube 830 is used (e.g., the angle is 10 degrees for the first face 800A, but the angle for the other faces of alignment cube 830, such as the second or third face 800B or 800C, will be greater than, or less than, 10 degrees). The angle can vary depending upon which alignment cube is used in the set of alignment cubes (e.g., the is 10 degrees for the alignment cube 830, but the angle for other guide cubes will be greater than, or less than, 10 degrees). The angle for the alignment block 630 or the alignment cube 830 can vary in increments of 0.25 degrees, 0.5 degrees, 1 degree, 5 degrees, or 10 degrees, but other increments are possible. The alignment block 630 and the alignment cube 830, or the set of alignment blocks or set of alignment cubes, can be used with a first patient and reused with subsequent patients after sanitizing.

FIG. 9 a side view of another example of an adjustable orthopedic system 900 including another alignment cube 930 and an alignment unit 950. The alignment cube 930 can be used to set relative guide plates between components of the alignment unit 950. The alignment unit 950 can include a guide plate 951 and an axis guide 952. The axis guide 952 can include a second guide wire bore 953.

The alignment cube 930 can include a first guide wire bore 910. The guide wire bore 910 can be configured to receive a guide wire 915 (e.g., a rigid cylinder used for surgical procedures). The alignment cube 930 can include features similar to the alignment cube 830 or the alignment block 630. The guide wire 915 can extend orthogonally from a face 905 of the alignment cube 930. The alignment cube 930 can have one or more slots, such as a slot 920. The one or more slots can be configured to have one or more inclined planes, such as inclined plane 940. In an example, the guide plate 951 and the guide wire 915 can be mated with the alignment cube 930. The guide wire 915 extends orthogonally from the face 905 and through the guide wire bore (e.g., the guide wire bore 1020 of FIG. 10) of the guide plate 951.

The guide plate 951 can be mated with the inclined plane 940 of a slot. The inclined plane 940 imparts an angle Θ to the guide plate 951 relative to the face 905. The relative angle Θ between the guide plate 951 and the face 905 can be the same as the relative angle between the guide plate 951 and the guide wire 915. The guide wire 915 can be able to extend through the guide plate 951 at an angle because the first guide wire bore (not shown) of the guide plate 951 can be configured to allow the guide wire 915 to translate through the guide plate 951 in one or more orientations.

In an example, the guide plate 951 can be mated with the alignment cube 930 and the guide wire 915 can be mated with the alignment cube 930 and translated through the guide plate 951. The guide plate 951 has an angle relative to the alignment cube 930. The guide plate 951 has an angle (e.g., 1, 2, 5, 10, 15, 25, or 90 degrees) relative to the guide wire 915.

The axis guide 952 can include the second guide wire bore 953. The second guide wire bore 953 can be configured to receive a guide wire (e.g., the guide wire 915) in a single orientation (e.g., the axis guide can be able to translate or slide along the guide wire). The reception of the guide wire by the axis guide 952 can make a longitudinal axis of the guide wire collinear with a longitudinal axis of the second guide wire bore 953.

The axis guide 952 can include a head 954. The head 954 can be configured to mate with, or couple with, a socket (e.g., socket 1010 of FIG. 10) of the guide plate 951. The mating of the head 954 and the socket can allow for a fixable positioning of the axis guide 952 relative to the guide plate 951. In an example, the guide plate 951 can be mated with a slot of the alignment cube 930 and can be oriented at a first angle with respect to a face of the alignment cube 930. The relative angle between the axis guide 952 and the guide plate 951 can be the first angle when a guide cube can be used in combination with the guide plate 951 and the axis guide 952. The axis guide 952 can be translated along the guide wire 915 and brought into communication with the socket of the guide plate 951. The axis guide 952 can require a predetermined force (e.g., a surgeon applying a force, such as a hammer strike, to an end of the axis guide 952) to mate, or couple, the axis guide 952 with the guide plate 951.

The positionable mating of the axis guide 952 and the guide plate 951 can allow for the position, or orientation, of the axis guide 952 relative to the guide plate 951 to remain temporarily fixed, or unchanged, once the position or orientation has been established or set, such as by a surgeon using a alignment cube 930. Because the axis guide was translated over the guide wire 915 and the guide wire 915 can be at the first angle relative to the guide plate, the positionable mating of the axis guide 952 with the guide plate 951 can set the relative angles between the axis guide 952 and the guide plate 951 at the first angle. The axis guide 952 and the guide plate 951 can have more than one relative angle set. In an example, the first angle can be in a first plane. The axis guide 952 and the guide plate 951 can be set at a second angle along a second plane. The first plane can be different than the second plane. The first plane can be orthogonal to the second plane. Additional relative angles and planes are capable of being used with the axis guide 952 and the guide plate 951. The mated (e.g., coupled) axis guide 952 and the guide plate 951 can be removed (e.g., decoupled) from the alignment cube 930 and the guide wire 915 as the alignment unit 950. The alignment unit 950 can maintain the relative angles between the axis guide 952 and the guide plate 951 that were set using the alignment cube 930.

FIG. 10 is a posterior view of an example of the adjustable orthopedic system 900 of FIG. 9 showing the alignment unit 150 coupled with an anatomical feature 1000. The anatomical feature 1000 can be a scapula or a hip bone. The alignment unit 950 can include an axis guide 952 and a guide plate 951. The guide plate 951 can include a guide wire bore configured to allow a guide wire to translate through the guide wire bore in one or more orientations. The relative angles between the axis guide 952 and the guide plate 951 can remain fixed once they have been set, such as through the interaction of one or more surface features on a head 954 of the axis guide and a socket 1010 of the axis guide 120. In an example, the alignment unit 950 can be used to install a guide wire in a patient's anatomical feature (e.g., the anatomical feature 1000). The alignment unit 950 can allow for the guide wire to be installed at the relative angles that were established between the axis guide 952 and the guide plate 951.

As previously discussed, an individual (e.g., a radiologist, a surgeon, a nurse, or the like) can determine the anatomical geometry of a patient by performing medical imaging on an anatomical feature of the patient. In an example, x-ray images can be taken of the anatomical feature in various reference plan views (e.g., superior, anterior, medial, or the like). The anatomical geometry, such as the angular relationship of the anatomical feature with respect to another anatomical feature or the reference plan views, can be determined by the individual from the x-rays. The individual can use the alignment cube 930 (or the alignment block 630 of FIG. 6 or the alignment cube 830 of FIG. 8) to establish the relative angles between the guide plate 951 and the axis guide 952. The relative angles can be substantially similar (e.g., within 10 degrees) to the angular relationship determined from the x-rays. Use of x-rays and the alignment cube 930 can eliminate the need for more expensive forms of medical imaging. Use of x-rays and the alignment cube 930 can eliminate the need for fabricating a patient specific model of the anatomical feature. Fabrication of the patient specific model can be expensive.

Various Notes

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An anatomy simulator, comprising:
   a guide body having one or more faces;
   a first simulator socket forming a recess in a first face of the one or more faces that extends along a first plane, wherein:
   the first simulator socket is configured to receive a first plate having a bottom surface that extends along a second plane; and
   the first simulator socket includes a first base portion extending along a third plane and against which the bottom surface is configured to engage; and
   a bore extending from the base portion of the first simulator socket to an interior of the anatomy simulator along a central axis perpendicular to the first plane, wherein the bore is configured to receive an alignment mechanism;
   wherein the third plane of the first base portion is angled at a first angle with respect to the first plane of the first face.

2. The anatomy simulator of claim 1, wherein the guide body, the first simulator socket and the bore are monolithic such that the bore is fixed relative to the simulator socket and the guide body and the first plate and the alignment mechanism are configured to couple at one or more orientations such that coupling the first plate with the alignment mechanism fixes the orientation of the first plate with respect to the alignment mechanism.

3. The anatomy simulator of claim 1, wherein the first simulator socket is configured to receive the first plate such that mating the first plate with the alignment mechanism and with the first base portion establishes the first angle between the first plate and the alignment mechanism.

4. The anatomy simulator of claim 3, wherein a portion of the alignment mechanism is quasi-spherical, and the quasi-spherical portion is configured to be received by a plate socket of the first plate.

5. The anatomy simulator of claim 4, wherein the quasi-spherical portion includes an expansion bore, wherein the expansion bore is configured to slidingly receive an expansion pin through an opening in the first plate, the expansion pin expanding the quasi-spherical portion from a first diameter to a second diameter.

6. The anatomy simulator of claim 4, wherein expanding the quasi-spherical portion from a first diameter to a second diameter couples the first plate with the alignment mechanism and fixes the orientation of the first plate with respect to the alignment mechanism.

7. The anatomy simulator of claim 1, wherein the first simulator socket is included in a plurality of simulator sockets and each of the one or more faces includes an individual simulator socket of the plurality of sockets.

8. The anatomy simulator of claim 1, further comprising simulator indicia on the first face configured to provide alphanumerical information identifying the first angle.

9. The anatomy simulator of claim 1, wherein the first socket includes one or more indicator portions configured to be aligned with an alignment indicia of the first plate.

10. The anatomy simulator of claim 1, wherein the first simulator socket is configured to extend along a central axis that is oblique to the first face.

11. The anatomy simulator of claim 1, wherein:
    the first face includes a first simulator indicia configured to provide alphanumerical information identifying the first angle;
    the first simulator socket includes a first indicator portion configured to receive an alignment indicia of the first plate; and
    wherein aligning the alignment indicia with the first indicator portion and mating the first plate with the anatomy simulator imparts the first angle onto the first plate with respect to the first face.

12. The anatomy simulator of claim 1, further comprising the first plate, the first plate comprising:
    a first plate surface configured to couple with an anatomical feature of a patient;
    a second plate surface opposite the first plate surface, a plate socket extending into the first plate surface; and
    a bore extending from the socket to the second guide plate surface.

13. An anatomy simulator system, comprising:
    a humeral head adapter comprising:
    a plate having a bottom surface; and
    a bore extending through the plate;

an alignment mechanism comprising:
  an expansion device comprising:
    an expandable ball configured to couple to the plate at the bore; and
    a stem connected to the expandable ball; and
  a pin receivable in the expandable ball; and
a monolithic guide body comprising:
  an alignment surface extending in a first plane and configured to mate with the bottom surface of the plate;
  a socket for receiving the stem of the alignment mechanism to hold the expansion device in a fixed position relative to the alignment surface, the socket extending along a first central axis disposed at an oblique angle to the first plane.

14. The anatomy simulator system of claim 13, wherein the plate and the alignment mechanism are configured to couple at one or more orientations and coupling the plate with the alignment mechanism fixes the orientation of the plate with respect to the alignment mechanism.

15. The anatomy simulator system of claim 13, wherein the expandable ball includes an expansion bore, wherein the expansion bore is configured to receive the pin to expand the expandable ball from a first diameter to a second diameter to couple the plate with the alignment mechanism and fix the orientation of the plate with respect to the alignment mechanism.

16. The anatomy simulator system of claim 13, wherein the socket is configured to receive the plate such that mating the plate with the alignment mechanism establishes a first angle between the plate and the alignment mechanism.

17. The anatomy simulator system of claim 16, further comprising simulator indicia on the monolithic guide body configured to provide alphanumerical information identifying the first angle.

18. The anatomy simulator system of claim 13, wherein the monolithic guide body includes a plurality of alignments surfaces and sockets each configured to set the plate relative to the alignment mechanism at a different angle.

19. The anatomy simulator system of claim 13, wherein the bore includes a plurality of lobes.

* * * * *